(12) United States Patent
Weiss et al.

(10) Patent No.: US 6,512,941 B1
(45) Date of Patent: Jan. 28, 2003

(54) MR METHOD FOR EXCITING THE NUCLEAR MAGNETIZATION IN A LIMITED VOLUME

(75) Inventors: Steffen Weiss, Hamburg (DE); Kai-Michael Lüdeke, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 82 days.

(21) Appl. No.: 09/718,251

(22) Filed: Nov. 22, 2000

(30) Foreign Application Priority Data

Nov. 25, 1999 (DE) .......................................... 199 56 595

(51) Int. Cl.[7] .............................................. A61B 5/05
(52) U.S. Cl. ...................... 600/410; 600/411; 600/410; 600/423; 600/424; 600/422; 324/300; 324/307; 324/309; 324/318
(58) Field of Search ................................. 600/407, 411, 600/419–424; 324/318; 128/899

(56) References Cited

U.S. PATENT DOCUMENTS

| | | | | |
|---|---|---|---|---|
| 4,572,198 A | * | 2/1986 | Codrington | 600/410 |
| 4,712,560 A | * | 12/1987 | Schaefer et al. | 324/309 |
| 5,353,795 A | * | 10/1994 | Souza et al. | 600/423 |
| 5,644,234 A | * | 7/1997 | Rasche et al. | 324/309 |
| 6,236,205 B1 | * | 5/2001 | Ludeke et al. | 324/300 |
| 6,263,229 B1 | * | 7/2001 | Atalar et al. | 324/318 |
| 6,280,385 B1 | * | 8/2001 | Melzer et al. | 324/318 |
| 6,397,094 B1 | * | 5/2002 | Ludeke et al. | 324/309 |

* cited by examiner

Primary Examiner—Marvin M. Lateef
Assistant Examiner—Barry Pass
(74) Attorney, Agent, or Firm—John Vodopia

(57) ABSTRACT

The invention relates to a method of and a device for exciting the nuclear magnetization in a limited volume of an object to be examined, utilizing a microcoil (L) which is present in the volume and is attached, for example, to an interventional instrument during the formation of a magnetic resonance image of the object to be examined. The excitation of the nuclear magnetization is performed by at least one RF pulse whose frequency spectrum does not overlap the range of the spin resonance spectrum, so that no nuclear magnetization is excited outside the close range of the microcoil in the object to be examined. The microcoil, however, is provided with an active or passive circuit (for example, it is wired together with at least one capacitance (C) and a non-linear component (D1, D2) so as to form a non-linear resonant circuit) which locally generates an RF signal from the RF pulse. The RF signal overlaps the spin resonance frequency and causes excitation of the nuclear magnetization exclusively in the close range of the microcoil. After measurement and appropriate signal processing, this nuclear magnetization is used either to determine the position of the microcoil for reproduction in the MR image of the object to be examined or to form an MR image of the close range of the microcoil. The invention also relates to a medical instrument for use in conjunction with the method.

13 Claims, 2 Drawing Sheets

MR METHOD FOR EXCITING THE NUCLEAR MAGNETIZATION IN A LIMITED VOLUME

BACKGROUND OF THE INVENTION

The invention relates to an MR method (MR=Magnetic resonance) for exciting the nuclear magnetization in a limited volume of an object to be examined, utilizing a microcoil which is present in said volume and is subject to at least one RF pulse. The invention also relates to a device for carrying out the method disclosed in claim 1 and to a preferably medical instrument for use in conjunction with the method and with the device.

A method and a device of this kind are known from EP-A 928 927. Therein, a capacitance is connected parallel to the microcoil so that a resonant circuit is obtained which is tuned essentially to the frequency of the RF pulses (RF= Radio Frequency). The (external) magnetic field produced by the RF pulses and traversing the object to be examined is intensified in the close range of the microcoil and its phase is shifted. As a result, the excitation of the nuclear magnetization is intensified in this close range, so that in the MR image this range is highlighted relative to the other parts of the object to be examined.

The excitation of the nuclear magnetization in a limited volume can be utilized in various ways; one possibility consists in forming an MR image of this strictly limited volume, for example a blood vessel. Restricting the MR image to a small volume results in short measuring times and enables fluoroscopic applications. Another possibility consists in the localization of the microcoil and possibly an instrument connected thereto. The instrument, for example a medical instrument at the location to be marked is then provided with a microcoil.

The acquisition of the MR signals for the imaging of a limited volume or for the localization of the microcoil can be performed in a comparatively simple and fast manner. However, MR signals are then received from the entire volume in which the conditions for magnetic resonance are satisfied. This volume is substantially larger than the close range in which the magnetic field of the microcoil is essentially concentrated. Consequently, aliasing artefacts occur in the MR images of the close range; in the case of localization by means of three orthogonal projection measurements, this results in a signal background which could make localization impossible.

SUMMARY OF THE INVENTION

Therefore, it is an object of the invention to conceive a method of the kind set forth in such a manner that the excitation of the nuclear magnetization is better restricted to the close range of the microcoil. It is a further object to provide an MR apparatus for carrying out the method as well as an instrument which is especially intended for use in conjunction with the method and the device.

This object is achieved by a method which includes the following steps: generating an RF pulse with a frequency spectrum which does not overlap the Larmor frequency, so that the nuclear magnetization in the object to be examined is not excited thereby, generating an additional frequency spectrum by a microcoil under the influence of the RF pulse, which additional frequency spectrum overlaps the Larmor frequency in such a manner that the nuclear magnetization is excited in a prescribed range, referred to herein as the close range, of the microcoil within a limited volume of the overall volume, as further discussed herein.

According to one embodiment of the invention, nuclear magnetization beyond the prescribed range of the microcoil cannot be excited. This occurs because the conditions for magnetic resonance are not satisfied beyond the prescribed range due to the specific spectrum of the RF pulse modified according to the invention. Due to the modification of the spectrum by the microcoil, the conditions for magnetic resonance are satisfied only in the prescribed range (i.e., close range) of the microcoil. Consequently, nuclear magnetization can be excited only in the close range. The invention thus offers the advantage that the MR signals practically do no contain any background signal originating from the overall volume, so that the problems of the method known thus far are avoided because of the essentially higher signal contrast.

In one embodiment, the invention discloses an MR apparatus which is suitable for carrying out the method according to the invention. Another embodiment describes a medical instrument which is particularly suitable for use in conjunction with a method or a device according to the invention. In the latter embodiment, the medical instrument includes a microcoil which is intended for localization in an object to be examined, the microcoil being wired so as to form a non-linear resonant circuit.

Additional embodiments disclose various possibilities for the acquisition of information from the spatially limited excitation of the nuclear magnetization. For example, one method is disclosed wherein the nuclear magnetization is excited alternately in the close range and in a larger volume enclosing said close range. As a result, additionally MR signals are acquired for an MR image in which the position resulting from the localization can be visualized, if desired. The alternating acquisition of MR signals for imaging and for localization is advantageous notably in the case of moving objects, because the imaging and the localization relate to practically the same time interval. In order to enhance the motional resolution, the duration and the frequency of the two operations (that is, the in duty cycle) can be advantageously adapted to one another.

According to one embodiment, anti-parallel connected diodes provide means which non-linearly co-operate with the microcoil. The microcoil couples with the anti-parallel connected diodes in such a manner so as to form a non-linear resonant circuit. Alternatively, a miniaturized circuit generates a signal having the Larmor frequency in response to a reception of signals having a frequency beyond the Larmor frequency.

BRIEF DESCRIPTION OF THE DRAWING FIGURES

Further details, characteristics and advantages of the invention will become apparent from the following description of a preferred embodiment which is given with reference to the drawing. Therein:

DETAILED DESCRIPTION OF INVENTIVE EMBODIMENTS

Figure 1:
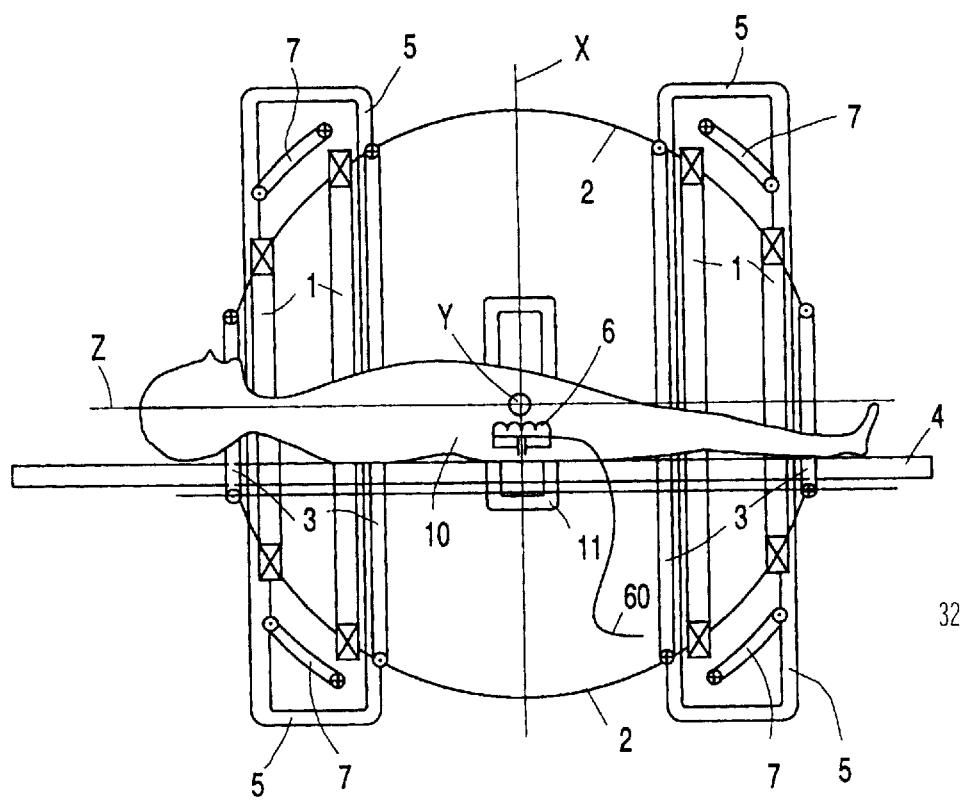
FIG. 1 is a strongly simplified representation of a device for generating MR images.

The device for forming MR images which is shown in FIG. 1 is also referred to as an MR examination apparatus and includes an arrangement of four main coils 1 for generating a uniform, steady magnetic field in the z direction (main field) whose magnetic flux density (magnetic induction) may be of the order of magnitude of from some tenths of Tesla to some Tesla. The main coils 1 are concentrically arranged relative to the z axis and may be situated on a spherical surface 2. Inside these coils there is arranged an object to be examined, for example a patient 10 positioned on a table top 4.

In order to generate a first gradient magnetic field which extends in the direction of the z axis and linearly varies in this direction there are provided four first coils 3 which are arranged on the spherical surface 2 or on a cylindrical surface. Also provided are four second coils 7 which generate a second gradient magnetic field which also extends in the direction of the z axis but varies linearly in the vertical direction (x direction). Finally, four third coils 5 (only two of which are shown) generate a third gradient magnetic field which extends in the direction of the z axis and linearly varies in the direction perpendicular to the plane of drawing of FIG. 1 (y direction).

A medical instrument 60 (for example, a catheter) has been introduced into the part of the patient to be examined; at the tip of the instrument there is provided a microcoil. This area is enveloped by an RF transmitter coil 11 which can be exposed to an RF pulse and produces an RF magnetic field exciting spin resonance in this area. The relaxation succeeding this excitation causes a change of the magnetization states which induces a corresponding voltage in an RF receiver coil 12 (see FIG. 2); this voltage is used for MR imaging where the gradient magnetic fields enable localization of the excited states.

Figure 2:
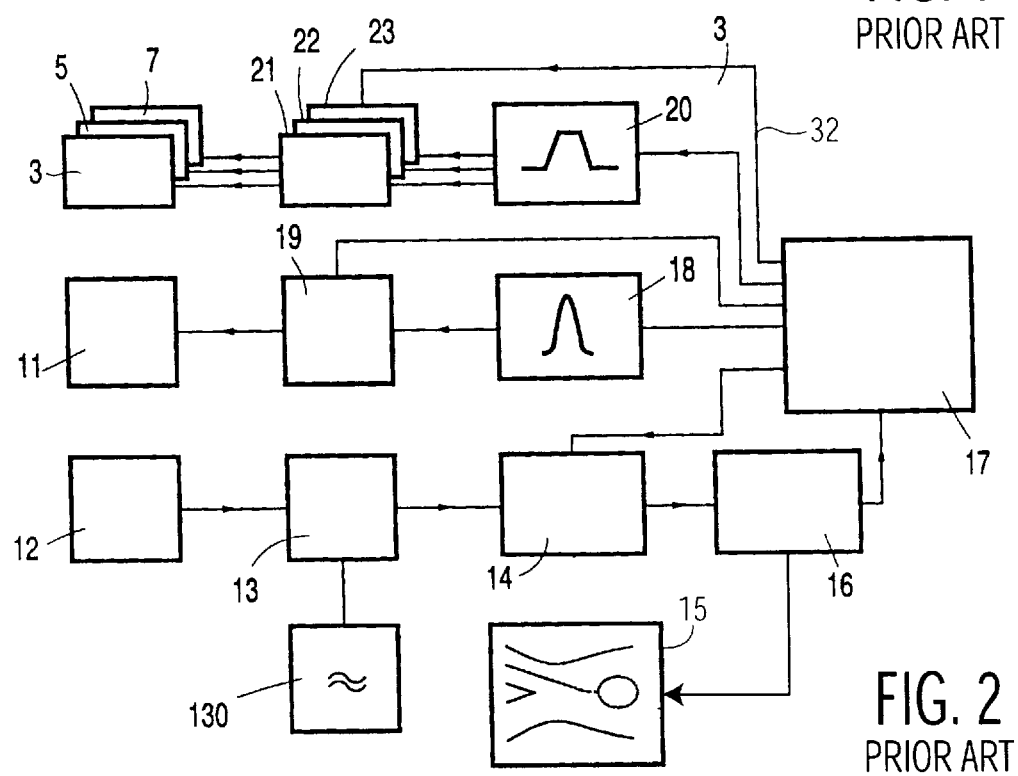
FIG. 2 shows a block diagram of such a device.

FIG. 2 shows diagrammatically the components which are of essential importance to the operation of this device, including a control unit 17 which controls a gradient waveform generator 20, a first gradient amplifier 21, a second gradient amplifier 22 and a third gradient amplifier 23 being connected to respective outputs of said generator. These generators generate the respective currents for the first coil 3, the second coil 5, and the third coil 7. The gain factors of these amplifiers are independently adjustable by the control unit 17, via leads 32, so that the coils 3, 5, 7 generate the gradient fields in the z, y and x directions, thus enabling slice selection in the corresponding three spatial directions in the zone examined.

Furthermore, the control unit 17 controls an. RF generator 18 in order to tune on the one hand the frequency of the RF pulses to the Larmor frequencies, being dependent on the gradient fields, for MR imaging on the one hand and for switching over the frequency in order to localize the microcoil on the other hand, in such a manner that magnetic resonance is excited only in the close range thereof. The RF pulses are applied to an amplifier 19 whose gain is controlled by the control unit 17 and ultimately reach the RF transmitter coil 11.

The MR signals induced in the RF receiver coil 12 due to the relaxation of the excited magnetization states are demodulated in a quadrature demodulator 13 by mixing with two 90° mutually offset carrier oscillations (having a Larmor or MR frequency determined by the local strength of the steady magnetic fields) from an oscillator 130, so that two signals are formed which may be considered as the real part and the imaginary part of a complex signal. These signals are applied to an analog-to-digital converter 14. Finally, the MR images are reconstructed in known manner by means of an image processing unit 16 so as to be displayed on a monitor 15.

Figure 3:
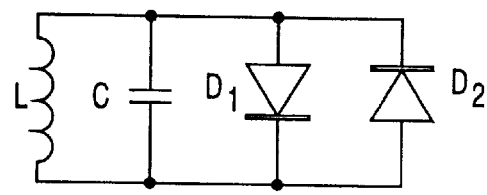
FIG. 3 shows an embodiment of a microcoil wired so as to form a non-linear resonant circuit.

FIG. 3 shows the microcoil L as well as, by way of example, the wiring of this coil so as to form a non-linear passive resonant circuit. This resonant circuit includes a capacitance C which is connected parallel to the coil L as well as two anti-parallel connected diodes $D_1$, $D_2$ which produce the non-linearity. Instead of the diodes, of course, other elements can be used for this purpose. The overall resonant circuit is preferably realized by means of miniaturized components so that it can be arranged completely at the tip of a medical instrument 60 to be introduced into the zone to be examined without external connection leads being required. The microcoil operates passively, that is, there are no leads from the microcoil to the outside; such leads always involve the risk of inducing voltages or currents which are detrimental to the patient.

Figure 4:
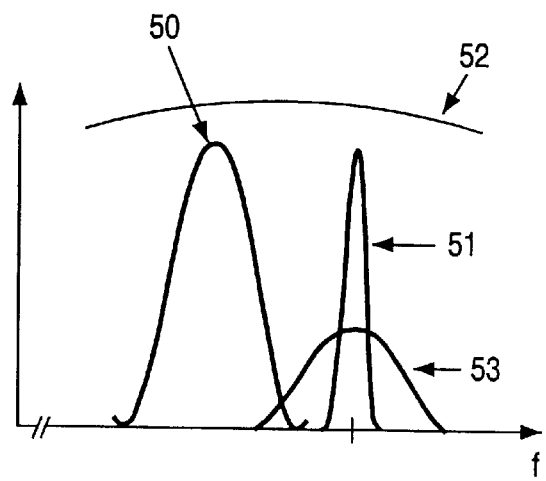
FIG. 4 shows a diagram of various frequencies.

The non-linearity introduced into the resonant circuit enables significantly more reliable localization of the medical instrument 60, supporting the microcoil L, in the examination zone on the basis of the projection measured signals which are now free from background. This operation is based on the relative position of the various frequency ranges shown in FIG. 4. In order to localize the instrument 60, first the control unit 17 switches over the RF generator 18 in such a manner that the spectrum 50 of the RF transmission pulse lies outside the spectrum 51 around the Larmor frequency, so that no ("overall") spin resonance as required for MR imaging is excited in the zone to be examined. At the same time, however, the spectrum 50 of the RF transmission pulse lies within the essentially wider resonant frequency range 52 of the resonant circuit.

The shifted spectrum of the RF transmission pulse 50 and the non-linearity induced in the resonant circuit, for example, by the anti-parallel connected diodes ($D_1$, $D_2$) are selected in a manner such that the non-linearity generates locally. That is, the non-linearity of the resonant circuit produces a frequency spectrum 53 locally, only in a close range of the microcoil. The frequency spectrum 53 is shown in idealized form in FIG. 4. Note that the frequency spectrum 53 also overlaps the Larmor frequency of the spectrum 51. This local excitation spectrum, or the corresponding current flowing through the resonant circuit, suffices to generate a magnetic flux density in the close range of the microcoil which excites the spin resonance.

Figure 5:
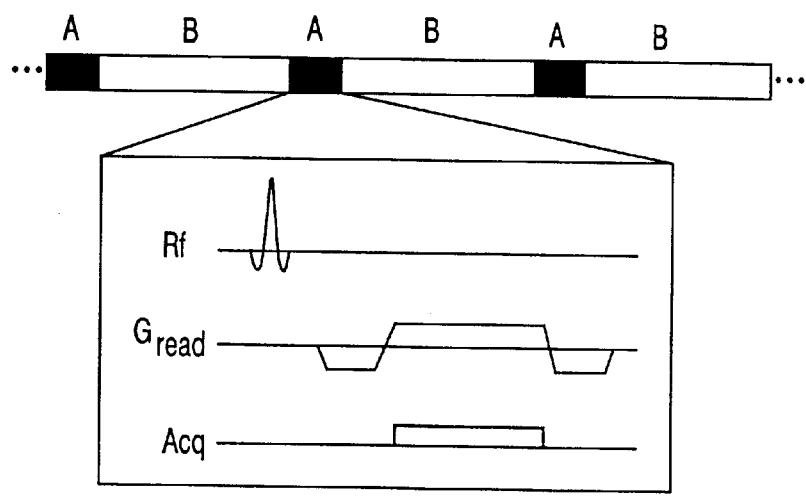
FIG. 5 shows diagrammatically a number of sequences during MR imaging and localization of a microcoil.

The localization of this spin resonance, and hence of the microcoil L or the medical instrument, is performed in conformity with FIG. 5 by the acquisition of the MR signals resulting from the excitation in essentially the same manner as for the MR imaging after the excitation of the spin resonance in the entire zone to be examined. In the case of three-dimensional localization, a spin or gradient echo signal evaluation can be performed, preferably without performing slice selections and phase encoding, by applying merely a read-out gradient magnetic field in one of the three spatial directions (frequency-encoded magnetic field) in order to evaluate the acquired signal by Fourier transformation in respect of the amplitudes of the frequency components in the relevant direction. This measurement and evaluation are performed alternately for all three spatial directions and in an alternating fashion with the measurement for the MR imaging (during which the spectrum of the RF pulse overlaps the Larmor frequency in the volume to be imaged) in order to determine the three-dimensional position quasi simultaneously with the formation the MR image. As an alternative for the described projection method, the measurement of the nuclear magnetization excited in the close range of the microcoil can also be performed by means of any other suitable method.

FIG. 5 shows, by way of example, a frequency-shifted RF pulse Rf and therebelow the variation of a gradient magnetic field $G_{read}$ for the gradient echo signal evaluation as well as an evaluated signal Acq for the localization.

As is clearly shown in FIG. 5, the processes A for the localization of the microcoil and B for the MR imaging of the object to be examined can be alternately performed, so that two interleaved sequences A, B, A, B, . . . are obtained. The length of the two operations A, B, that is the repetition rate of the sequences as well as their duty cycle, can be selected almost arbitrarily in dependence on the relevant application, notably the speed of motion of the microcoil, on the medium to be imaged as well as on the desired motional resolution. The localization may have a duration of, for example, 6 ms whereas 500 ms are used for the MR imaging.

Furthermore, during a localization operation either a complete three-dimensional determination of the position of the microcoil may be performed or only the position is determined in one direction during each operation, so that the position of the microcoil is obtained only after three localization operations.

According to another embodiment, the microcoil can be configured for use in the imaging of a strictly limited volume, for example, a blood vessel. In such an embodiment, the microcoil method is configured to use an RF transmission pulse with a frequency-shifted spectrum in combination with an arbitrary imaging MR method, wherein the arbitrary imaging MR method is adapted to the imaging in the strictly limited volume.

What is claimed is:

1. An MR method for exciting nuclear magnetization in a limited volume of an object to be examined, utilizing a microcoil which is present in said limited volume and is subject to at least one RF pulse, comprising:

generating the RF pulse with a frequency spectrum which does not overlap the Larmor frequency, so that a nuclear magnetization in the object to be examined is not excited thereby; and generating an additional frequency spectrum by the microcoil under the influence of the RF pulse, wherein the additional frequency spectrum overlaps the Larmor frequency in such a manner that the nuclear magnetization is excited within a prescribed range of the microcoil present in said limited volume.

2. An MR method as claimed in claim 1, wherein the nuclear magnetization excited within the prescribed range of the microcoil is used to localize the microcoil.

3. An MR method as claimed in claim 2, further comprising:

generating a series of sequences to acquire an MR image of a volume of the object to be examined, wherein the volume of the object to be examined is larger than the prescribed range of the microcoil, wherein measurements required for the localization of the microcoil are performed so as to alternate with the excitation of the nuclear magnetization for the larger volume, wherein the localization is restricted to the prescribed range of the microcoil within the larger volume.

4. An MR method as claimed in claim 1, wherein the nuclear magnetization excited in the prescribed range of the microcoil is reproduced in an MR image.

5. An MR apparatus for carrying out the method in claim 1, including a magnet for generating a uniform, steady magnetic field whose strength defines the Larmor frequency, means for generating RF pulses, and means for receiving MR signals generated in the object to be examined, wherein the MR apparatus further includes a control device for controlling the frequency spectrum of the RF pulses in such a manner that no nuclear magnetization is excited thereby in the object to be examined, that the frequency spectrum of the RF pulse is modified, utilizing an active or passive circuit connected to the microcoil, in the prescribed range of the microcoil in such a manner that the modified frequency spectrum overlaps the Larmor frequency, and that MR signals arising in the prescribed range of the microcoil can be received by the receiving means.

6. An instrument for use in conjunction with a device as claimed in claim 5, wherein the microcoil is provided with non-linearly operating means.

7. An instrument as claimed in claim 6, wherein the microcoil is wired so as to form a non-linear resonant circuit.

8. An instrument as claimed in claim 7, wherein the resonant circuit includes two antiparallel connected diodes ($D_1$, $D_2$) which induce its non-linearity.

9. An instrument as claimed in claim 7, wherein the resonant circuit is attached to the instrument in the form of a miniaturized module.

10. An instrument for use in conjunction with a method as claimed in claim 1 wherein the instrument includes a microcoil provided with non-linearly operating means.

11. An instrument as claimed in claim 10, wherein the microcoil is wired so as to form a non-linear resonant circuit.

12. An instrument as claimed in claim 11, wherein the resonant circuit includes two antiparallel connected diodes ($D_1$, $D_2$) which induce its non-linearity.

13. An instrument as claimed in claim 11, wherein the resonant circuit is attached to the instrument in the form of a miniaturized module.

* * * * *